(12) United States Patent
    Kusens

(10) Patent No.: US 9,159,215 B1
(45) Date of Patent: Oct. 13, 2015

(54) METHOD FOR DETERMINING WHETHER AN INDIVIDUAL LEAVES A PRESCRIBED VIRTUAL PERIMETER

(71) Applicant: Neil Kusens, Sherman Oaks, CA (US)

(72) Inventor: Neil Kusens, Sherman Oaks, CA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

(21) Appl. No.: 14/084,588

(22) Filed: Nov. 19, 2013

Related U.S. Application Data

(63) Continuation-in-part of application No. 13/543,816, filed on Jul. 7, 2012.

(60) Provisional application No. 61/507,088, filed on Jul. 12, 2011, provisional application No. 61/798,964, filed on Mar. 15, 2013.

(51) Int. Cl.
    G08B 23/00        (2006.01)
    *G08B 21/22*      (2006.01)
    *G08B 3/00*       (2006.01)

(52) U.S. Cl.
    CPC . *G08B 21/22* (2013.01); *G08B 3/00* (2013.01)

(58) Field of Classification Search
    CPC .... G08B 21/02; G08B 21/18; G08B 13/2462; G08B 21/0202; A01K 11/006; A61B 5/0022; A61B 5/0024; A61B 5/1117; G01S 5/0027

USPC ............. 340/573.1, 573.4, 573.7, 540, 686.1, 340/539.1, 500; 702/188; 700/28, 32
    See application file for complete search history.

(56) References Cited

U.S. PATENT DOCUMENTS

| | | | |
|---|---|---|---|
| 5,448,221 A * | 9/1995 | Weller | 340/539.21 |
| 6,160,478 A * | 12/2000 | Jacobsen et al. | 340/539.12 |
| 6,614,349 B1 * | 9/2003 | Proctor et al. | 340/572.1 |
| 2007/0085690 A1 * | 4/2007 | Tran | 340/573.1 |
| 2007/0279219 A1 * | 12/2007 | Warriner | 340/539.23 |
| 2008/0002860 A1 * | 1/2008 | Super et al. | 382/114 |
| 2009/0278934 A1 * | 11/2009 | Ecker et al. | 348/152 |
| 2009/0322513 A1 * | 12/2009 | Hwang et al. | 340/539.12 |
| 2010/0176952 A1 * | 7/2010 | Bajcsy et al. | 340/573.1 |
| 2010/0205771 A1 * | 8/2010 | Pietryga et al. | 16/2.2 |
| 2010/0285771 A1 | 11/2010 | Peabody | |
| 2011/0025493 A1 * | 2/2011 | Papadopoulos et al. | 340/539.12 |
| 2011/0087079 A1 * | 4/2011 | Aarts | 600/300 |
| 2011/0087707 A1 | 4/2011 | Aarts | |

OTHER PUBLICATIONS

Pending U.S. Application by same inventor Neal Kusens, U.S. Appl. No. 13/543,816, filed Jul. 7, 2012, entitled "Method and Process for Determining Whether an Individual Suffers a Fall Requiring Assistance".

(Continued)

*Primary Examiner* — Kerri McNally
(74) *Attorney, Agent, or Firm* — Daniel S. Polley, P.A.

(57) ABSTRACT

A method and system that allows healthcare providers, hospitals, skilled nursing facilities and other persons to monitor disabled, elderly or other high-risk individuals to prevent or reduce falls and/or mitigate the impact of a fall by delivering automated notification of "at risk" behavior and falls by such an individual being monitored where assistance is required.

18 Claims, 2 Drawing Sheets

Virtual Safety Rails Configuration, Monitoring and Alerting

(56) References Cited

OTHER PUBLICATIONS

Pending U.S. Application by same inventor Neal Kusens, U.S. Appl. No. 14/575,850, filed Dec. 18, 2014, entitled "Method and Process for Determining Whether an Individual Suffers a Fall Requiring Assistance".

Pending U.S. Application by same inventor Neal Kusens, U.S. Appl. No. 14/599,498, filed Jan. 17, 2015, entitled "Method and System for Determining Whether an Individual Takes Appropriate Measures to Prevent the Spread of Healthcare Associated Infections".

Pending U.S. Application by same inventor Neal Kusens, U.S. Appl. No. 14/611,363, filed Feb. 2, 2015, entitled "Method and System for Determining Whether an Individual Takes Appropriate Measures to Prevent the Spread of Healthcare Associated Infections".

Pending U.S. Application by same inventor Neal Kusens, U.S. Appl. No. 14/613,856, filed Feb. 4, 2015, entitled "Method and System for Determining Whether an Individual Takes Appropriate Measures to Prevent the Spread of Healthcare Associated Infections Along With Centralized Monitoring".

Pending U.S. Application by same inventor Neal Kusens, U.S. Appl. No. 14/623,349, filed Feb. 16, 2015, entitled "Method for Determining Whether an Individual Enters a Prescribed Virtual Zone Using 3D Blob Detection".

Pending U.S. Application by same inventor Neil Kusens, U.S. Appl. No. 14/743,447, filed Jun. 18, 2015, entitled "System for Determining Whether an Individual Suffers a Fall Requiring Assistance".

Pending U.S. Application by same inventor Neil Kusens, U.S. Appl. No. 14/743,499, filed Jun. 18, 2015, entitled "System for Determining Whether an Individual Suffers a Fall Requiring Assistance".

Pending U.S. Application by same inventor Neil Kusens, U.S. Appl. No. 14/743,264, filed Jun. 18, 2015, entitled "System for Determining Whether an Individual Enters a Prescribed Virtual Zone Using 3D Blob Detection".

Pending U.S. Application by same inventor Neil Kusens, U.S. Appl. No. 14/727,434, filed Jun. 1, 2015, entitled Method for Determining Whether Enters a Prescribed Virtual Zone Using Skeletal Tracking and 3D Blob Detection.

Pending U.S. Application by same inventor Neil Kusens, U.S. Appl. No. 14/728,762, filed Jun. 2, 2015, entitled "Method for Determining Whether an Individual Leaves a Prescribed Virtual Perimeter".

Pending U.S. Application by same inventor Neil Kusens, U.S. Appl. No. 14/724,969, filed May 29, 2015, entitled "Method and Process for Determining Whether an Individual Suffers a Fall Requiring Assistance".

* cited by examiner

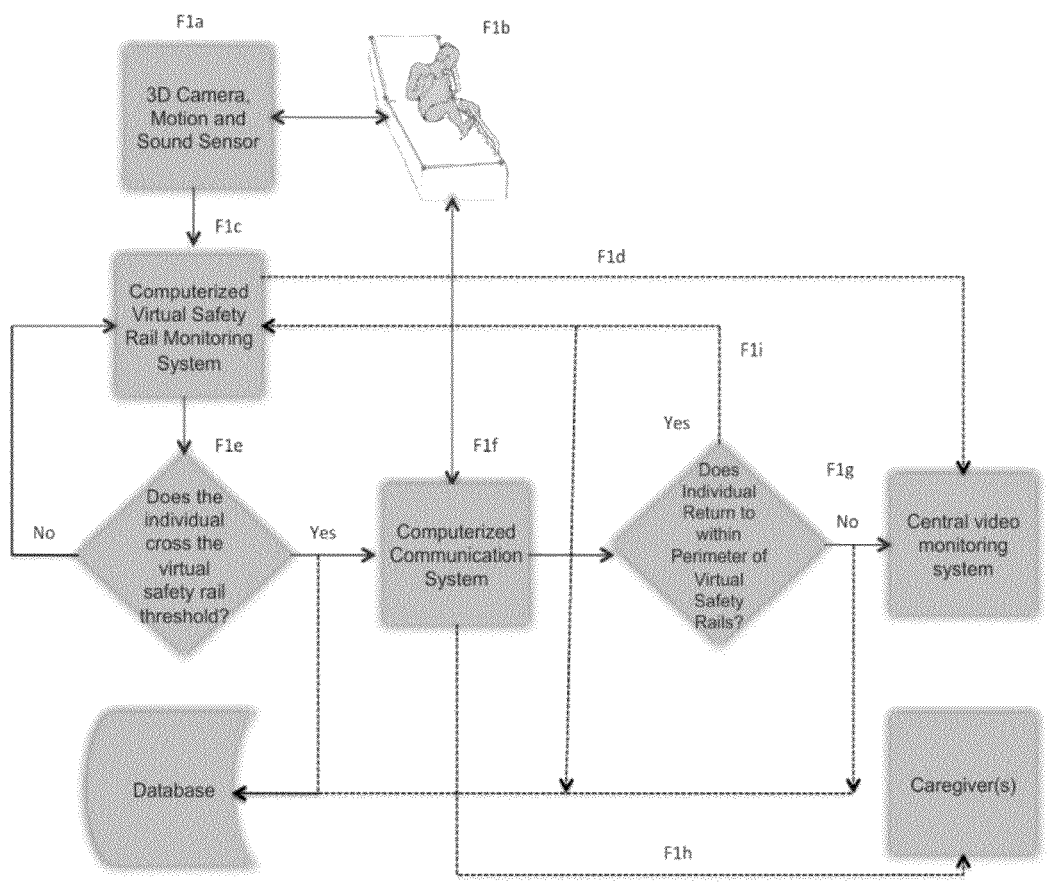
FIGURE 1: Virtual Safety Rails Configuration, Monitoring and Alerting

FIGURE 2: Centralized Video Monitoring System
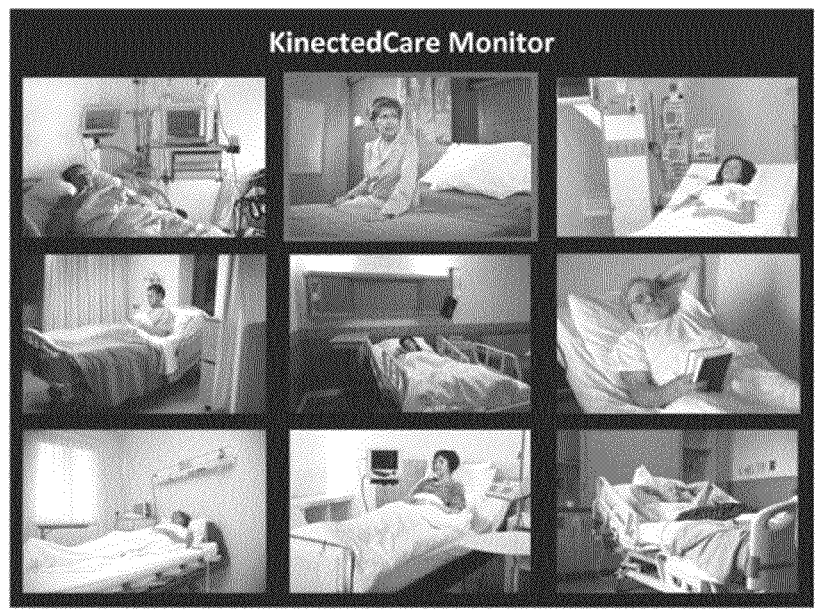

METHOD FOR DETERMINING WHETHER AN INDIVIDUAL LEAVES A PRESCRIBED VIRTUAL PERIMETER

This application is a continuation-in-part of U.S. application Ser. No. 13/543,816, filed Jul. 7, 2012, which claimed priority to and the benefit of U.S. Application Ser. No. 61/507,088, filed Jul. 12, 2011 and this application also claims priority to and the benefit of U.S. Application Ser. No. 61/798,964, filed Mar. 15, 2013, all of the above applications are incorporated by reference in their entireties.

FIELD OF THE INVENTION

The present invention is generally directed to patient monitoring systems and particularly to a system and method for monitoring patients in a manner which prevents or reduces patient falls.

BACKGROUND

According to recent studies, falls are a leading cause of death among people over the age of 65 years and 10% of the fatal falls for patients over 65 years of age occur in a hospital setting. For the general population, studies estimate that patient falls occur in 1.9 to 3% of all acute care hospitalizations. Of these hospital-based falls, approximately 30% will result in a serious injury with the cost to care for these injuries estimated to reach $54.9 billion per year by 2020. Current technologies that exist to assist in the prevention of falls are limited in their capabilities. These include pressure pads on the bed that trigger an alert when no pressure is detected on the pad, pressure pads on the floor and light beams that create a perimeter with alarms going off upon interruption of the beam. The pressure pads are ineffective as they do not prevent the fall but rather alert after the fact when it is too late. Additionally they are prone to false positive alerts. The light beams are also prone to false alerts when the patient or visitor simply reaches through it or the caregiver breaks the beam while delivering medication, food, drink or conducting a procedure on the patient. The present invention is directed to addressing these above-described shortcomings with current technology.

SUMMARY OF THE INVENTION

Generally disclosed is a novel method and system that allows healthcare providers, hospitals, skilled nursing facilities and other persons to monitor disabled, elderly or other high-risk individuals and utilize the described technology to prevent or reduce falls and/or mitigate the impact of a fall by delivering automated notification of "at risk" behavior and falls by such an individual being monitored where assistance is required.

The following non-limiting definitions are provided as aid in understanding the disclosed novel method and system:

| | |
|---|---|
| 3D Camera, Motion and Sound Sensor | An electronic device that contains one or more cameras capable of recording video and identifying individual objects, people and motion regardless of lighting conditions and which can also include one or more microphones to detect audio. |
| Computerized Virtual Safety Rail Monitoring System | A computer system specifically designed and programmed to create virtual safety rails around a specific object such as a hospital bed and which monitors activity based on information received from the 3D Camera, Motion and Sound sensor. |
| Computerized Communication System | A computer system specifically designed and programmed to facilitate communication between the monitored patient and computerized monitoring system in the event the virtual safety rails are crossed. |
| System Database | A computer database that stores records of all alerts generated, confirmation requests, responses, and reconfirmation requests. |
| Video Monitoring System | A monitor that displays a video feed and alerts from one or multiple 3D Camera, Motion and Sound Sensors. |
| Caregiver | A relative, friend, individual, company or facility whose purpose is to provide assistance in daily living activities for individuals who are disabled, elderly or otherwise in needs of assistance. |

BRIEF DESCRIPTION OF THE DRAWINGS

FIG. 1 is a block diagram of a virtual safety rails configuration, monitoring and alerting system and method in accordance with the present invention; and FIG. 2 is a non-limiting example of a centralized video monitoring system that can be used with the system and method shown in FIG. 1.

DETAILED DESCRIPTION OF THE INVENTION

FIG. 1 illustrates a block diagram for the virtual safety rails configuration, monitoring and alerting system and method of the present invention. Specifically, FIG. 1 shows the workflow for monitoring an individual's status through the use of one or more 3D Camera, Motion and Sound sensors.

At step F1a, one or more 3D Camera, Motion and/or Sound sensors can be installed in the patient's or individual's room. At step F1b, the one or more 3D Motion and Sound sensors can be configured to recognize the individual using biometric identifiers such as height, distance between points on the body, etc. Virtual safety rails can also be calibrated at this time. At step F1c, data from the 3D Motion and Sound sensors can be sent to a Computerized Virtual Safety Rail Monitoring System. At step F1d, a continuous video feed can be sent to the central Video Monitoring System.

At step F1e, if the computerized virtual safety rail monitoring system detects that the patient or any part of the patient has crossed outside of the designated perimeter (beyond the virtual safety rail), the monitoring system will alert the computerized communication system. A record can also be entered in a database to record the incident. If other individuals such as a caregiver are also detected at the time the virtual safety rail threshold is crossed, the system can be designed or programmed such that no alert is generated and it will continue to monitor the data being sent from the 3D camera, motion and sound sensor. Additionally, the system can be programmed to be capable of detecting pre-programmed hand, arm, leg and body gestures from the patient/individual and/or another person in the room to initiate an alert to the computerized communication system. As a non-limiting example, a particular hand gesture could be used as a signal to send medical assistance or that the individual needs to use the restroom. Further examples are numerous.

At step F1f, the computerized communication system preferably can first issue a verbal warning to the patient that they have crossed the virtual safety rail threshold. This verbal warning can be a pre-recorded message, including, but not limited to, a pre-recorded message from any caregiver, and will advise the patient to return to within the perimeter of the virtual safety rails. At step F1g, should the patient fail to return to within the perimeter of the virtual safety rails in a timely manner, an alert can be generated on the central Video Monitoring System (see FIG. 2). The system database can also be updated to reflect actions taken. The system can be designed to provide visual and/or audio alerts.

At step F1h, the computerized communication system can notify caregivers or other designated persons that the individual requires assistance. Notification of caregivers can be made through phone call, text messaging, speakerphone systems, pagers, email, or other electronic means of communication if so desired and configured. At step F1i, if the individual returns within the perimeter of the virtual safety rails, the system database can be updated to reflect such. Additionally, the system will continue to monitor the patient and store all data in the system database.

FIG. 2 shows a non-limiting example of a centralized video monitoring system that can be used with the system and method. The window highlighted in red is a non-limiting example of an alert that can be generated when the patient fails to return to within the perimeter of the virtual safety rails.

In one non-limiting embodiment, for operation the present invention can use the following components:
1. One or more 3D Camera, Motion and/or Sound Sensors
2. A Computerized Virtual Safety Rail Monitoring System
3. A Computerized Communication System
4. A Centralized Video Monitoring System; and
5. Database The various components can be in electrical and/or wireless communication with each other.

The automatic detection of an individual leaving a prescribed virtual perimeter will provide significant administrative and clinical benefits to caregivers and individuals alike, including the following non-limiting public benefits:
1. Automation of determination of perimeter violation and automated notification of caregivers or other designated entities.
2. Ability to alert patients and caregivers in time to prevent patient from getting out of bed
3. Reduction in response time for individuals who have fallen and require assistance.
4. Increased survival rate for individuals who have experienced a fall
5. Reduction in costs for hospitalization and medical care related to complications from a fall
6. Ability to distinguish multiple individuals and prevent false positives
7. Ability to distinguish direction of motion of prevent false positives
8. Ability to provide video feed of patient under all lighting conditions to the central video monitoring system
9. Audio and gesture based recognition to allow multiple forms of communication with patient.

Any computer/server/electronic database system (collectively "Computer System") capable of being programmed with the specific steps of the present invention can be used and is considered within the scope of the invention. Once programmed such Computer System can preferably be considered a special purpose computer limited to the use of two or more of the above particularly described combination of steps (programmed instructions) performing two or more of the above particularly described combination of functions.

All components of the present invention system and their locations, electronic communication methods between the system components, electronic storage mechanisms, etc. discussed above or shown in the drawings, if any, are merely by way of example and are not considered limiting and other component(s) and their locations, electronic communication methods, electronic storage mechanisms, etc. can be chosen and used and all are considered within the scope of the invention.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. A method for detecting when a monitored individual or any part of the monitored individual has crossed outside of a designated electronic perimeter, said method comprising the steps of:
   (a) electronically calibrating virtual safety rails defining a designated electronic perimeter within an area of a room;
   (b) configuring one or more 3D motion sensors to recognize a specific individual using one or more distances between points on the body for the specific individual or a height of the specific individual in order to monitor movements of the specific individual;
   (c) electronically receiving a continuous video feed by a computerized monitoring system from the one or more 3D motion sensors located in the room; and
   (d) electronically alerting a remote computerized communication system when the computerized monitoring system detects that the specific individual located in the room or any part of the specific individual has crossed over the designated electronic perimeter based on 3D information from the continuous video feed received from the one or more 3D motion sensors.

2. The method for detecting of claim 1 further comprising the step of electronically issuing an audible message to the individual by a computerized communication system to inform the individual that they have crossed the designated electronic perimeter.

3. The method for detecting of claim 1 further comprising the step of generating an alert on a central video monitoring system if the individual fails to return within the designated electronic perimeter within a predetermined period of time after first issuing an audible message to the individual to return within the electronic perimeter of the virtual safety rails.

4. The method for detecting of claim 1 further comprising the step of notifying a designated person associated with the individual that the individual did not return within the designated electronic perimeter.

5. The method of detecting of claim 1 wherein the computerized monitoring system detects that the designated electronic perimeter has been crossed by the specific individual by tracking points on the body of the specific individual from the continuous video feed received from the one or more 3D motion sensors, wherein detection by the computerized monitoring system is made in time to prevent the specific individual from getting out of bed.

6. A method for detecting when a monitored individual or any part of the monitored individual has crossed outside of a designated electronic perimeter, said method comprising the steps of:
   (a) providing one or more 3D motion and sound sensors within a room occupied by a specific individual to be monitored;
   (b) configuring the one or more sensors to recognize one or more distances between points on the body for the specific individual or a height of the specific individual in order to monitor movements of only the specific individual;
   (c) electronically calibrating virtual safety rails defining a designated electronic perimeter within an area of the room;
   (d) electronically forwarding a continuous video feed to a computerized monitoring system by the one or more sensors; and
   (e) electronically alerting a computerized communication system when the computerized monitoring system detects that the specific individual or any part of the specific individual has crossed over the designated electronic perimeter based on 3D information from the continuous video feed received from the one or more 3D motion and sound sensors.

7. The method for detecting of claim 6 further comprising the step of updating a database in communication with the computerized monitoring system regarding the detection of the individual or a part of the individual crossing over the designated electronic perimeter.

8. The method for detecting of claim 6 further comprising the step of notifying a previously designated contact by an electronic message informing the previously designated contact of the detected designated electronic perimeter crossing.

9. The method for detecting of claim 6 wherein no electronic alert is provided in step (e) if one or more other persons are detected to be in the room at the time the individual or a part of the individual crosses outside of the designated electronic perimeter though the computerized monitoring system continues to receive the continuous video feed from the one or more 3D motion and sound sensors.

10. The method for detecting of claim 6 further comprising the step of continuing to send the video feed from the one or more 3D Motion and sound sensors to the computerized monitoring system after it has been determined that the individual or a part of the individual has crossed outside of the designated electronic perimeter.

11. The method for detecting of claim 6 further comprising the step of electronically issuing an audible message to the individual by the computerized communication system to inform the individual that they have crossed the designated electronic perimeter.

12. The method for detecting of claim 11 wherein the audible message is a pre-recorded message.

13. The method for detecting of claim 12 wherein the pre-recorded message contains the voice of a caregiver associated with the individual.

14. The method for detecting of claim 12, wherein the pre-recorded message advises the individual to return within the designated electronic perimeter defined by the virtual safety rails.

15. The method for detecting of claim 6 further comprising the step of generating an alert on a central video monitoring system if the individual fails to return within the designated electronic perimeter within a predetermined period of time after first issuing an audible message to the individual to return within the electronic perimeter of the virtual safety rails.

16. The method for detecting of claim 15 wherein the alert is an audible alert or a visual alert.

17. The method for detecting of claim 15 further comprising the step of notifying a designated person associated with the individual that the individual did not return within the designated electronic perimeter.

18. A method for detecting when a monitored individual or any part of the monitored individual has crossed outside of a designated electronic perimeter, said method comprising the steps of:
   (a) providing one or more 3D motion and sound sensors within a room occupied by a specific individual to be monitored;
   (b) configuring the one or more sensors to recognize one or more distances between body points for the specific individual in order to monitor movements of only the specific individual;
   (c) electronically calibrating virtual safety rails defining a designated electronic perimeter within an area of the room;
   (d) electronically forwarding a continuous video feed to a remote computerized monitoring system by the one or more sensors; and
   (e) electronically alerting a computerized communication system when the remote computerized system detects that the specific individual or any part of the specific individual has crossed over the designated electronic perimeter by tracking points on a body of the specific individual from 3D information of the continuous video feed received from the one or more 3D motion and sound sensors, wherein detection by the remote computerized system is made in time to prevent the specific individual from getting out of bed.

* * * * *